United States Patent [19]

Morin, Jr. et al.

[11] Patent Number: 4,885,362
[45] Date of Patent: Dec. 5, 1989

[54] AZETIDINONE INTERMEDIATES FOR 1-CARBA(DETHIA)CAPHALOSPORINS

[75] Inventors: John M. Morin, Jr., Brownsburg; William C. Vladuchick, Indianapolis, both of Ind.

[73] Assignee: Eli Lilly and Company, Indianapolis, Ind.

[21] Appl. No.: 202,287

[22] Filed: Jun. 6, 1988

[51] Int. Cl.$^4$ .................. C07D 705/08; C07D 403/06; C07D 409/12; C07F 7/10
[52] U.S. Cl. .................................................. 540/364
[58] Field of Search .......................................... 540/364

[56] References Cited

U.S. PATENT DOCUMENTS

| | | | |
|---|---|---|---|
| 4,226,866 | 10/1980 | Christensen et al. | 424/248 |
| 4,407,815 | 10/1983 | Pearson | 514/210 |
| 4,665,171 | 5/1987 | Evans et al. | 540/364 |

OTHER PUBLICATIONS

Hatanaka et al., "A Simple Synthesis of (±)-1-Carbacephem Derivatives", *Tetrahedron Letters*, vol. 24 (No. 44), pp. 4837-4838, 1983.

*Primary Examiner*—Mark L. Berch
*Attorney, Agent, or Firm*—William B. Scanlon; Leroy Whitaker

[57] ABSTRACT

Azetidinone-2 intermediates represented by the formula

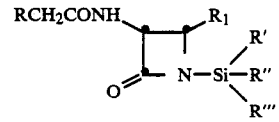

wherein R is phenyl, phenoxy or thienyl, $R_1$ is —CH═CH—COOR$_1$' wherein $R_1$' is an ester, e.g., benzyl; —CH$_2$CH$_2$COR$_2$ wherein $R_2$ is OH or imidazol-1-yl; —CH$_2$CH$_2$C(O)CH$_2$COOR$_1$' where $R_1$' is an ester, e.g., p-nitrobenzyl; and R', R" and R'" are $C_1$–$C_4$ alkyl, aryl or aralkyl; are converted to 1-carba(dethia)cephalosporin antibiotics. Preferably, R is phenoxy and the 1-silyl group is dimethyl-t-butylsilyl. Also provided is 3β-phenoxyacetylamino-4β-(2-carboxyethyl)azetidinone, likewise useful in the preparation of 1-carbacephalosporin antibiotics.

6 Claims, No Drawings

AZETIDINONE INTERMEDIATES FOR 1-CARBA(DETHIA)CAPHALOSPORINS

BACKGROUND OF THE INVENTION

This invention relates to β-lactam antibiotics. In particular, it relates to intermediates useful in the preparation of 1-carba(dethia)cephalosporin antibiotics.

In contrast to the cephalosporin antibiotics, which are prepared semi-synthetically, the 1-carba(dethia)-cephalosporins have thus far been obtained only by total synthetic methods. For example, Christensen et al., U.S. Pat. No. 4,226,866, describe a method for preparing 1-carba(dethia)cephalosporins. Also, Evans et al., in U.S. Pat. No. 4,665,171, describe an asymmetric total synthesis of the amino-protected 3-hydroxy-1-carba(dethia)cephalosporin nucleus ester. Because of the growing importance of the 1-carba(dethia)cephalosporins as possible therapeutic agents for the treatment of infectious diseases, intermediates useful in the preparation of such antibiotics are of considerable value.

SUMMARY

Azetidine-2-ones represented by the following formula 1 are provided

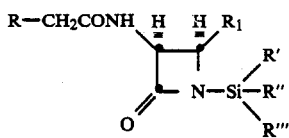

wherein R is phenyl, phenoxy or thienyl; $R_1$ is 2-carboxyvinyl, 2-carboxyethyl or 5-carboxypentane-3-one wherein the carboxy group may be esterified with a carboxy-protecting group; and R', R" and R"' are independently $C_1-C_4$ alkyl, aryl such as phenyl or aralkyl, e.g., benzyl, diphenylmethyl and triphenylmethyl.

The azetidinones 1 are valuable intermediates in the preparation of 1-carba(dethia)cephalosporins directly substituted in the 3-position by halogen or alkoxy. For example, 1-(dimethyl-t-butyl)silyl-3β-phenoxyacetylamino-4-(2-benzyloxycarbonylvinyl)-azetidin-2-one is hydrogenated to provide the correspondingly substituted 4-(2-carboxyethyl)azetidinone. The latter is reacted with carbonyl diimidazole to provide the correspondingly substituted 4-[2-(imidazol-1-yl-carbonyl)ethyl]azetidinone which, upon reaction with the magnesium salt of a malonic acid half ester, provides the azetidinone 1 wherein $R_1$ is an esterified 5-carboxypentane-3-one. The silyl group in the 1-position is removed, for example, with tetra-n-butylammonium fluoride to provide 3β-phenoxyacetylamino-4-(5-esterified carboxypentane-3-one)azetidinone. The above β-keto ester thus obtained is reacted with an arylsulfonyl azide to provide the α-diazo-β-keto ester which undergoes rhodium catalyzed cyclization to the bicyclic 1-carba(dethia)cephalosporin, 3β-phenoxyacetylamino-3-hydroxy-1-carba(dethia)-3-cephem-4-carboxylic acid ester.

DETAILED DESCRIPTION

The azetidinones 1 provided by this invention are intermediates employed sequentially in a process for preparing the 1-carba(dethia)cephalosporin as described hereinafter. These intermediates which are encompassed within the structural formula 1 are represented more particularly by the following structural formulas 1A, 1B and 1C.

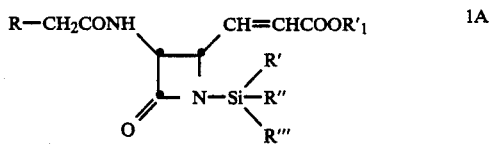

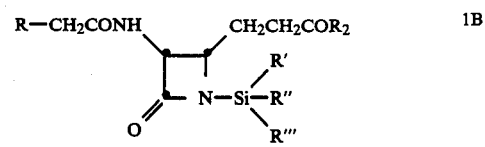

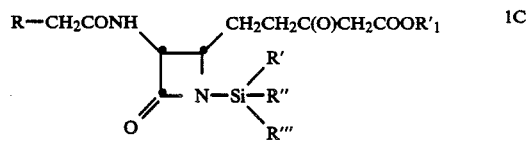

In the above formulas, R, R', R" and R"' have the same meanings as defined for formula 1 above, $R_1'$ is hydrogen or a benzyl, substituted benzyl or diphenylmethyl ester group and $R_2$ is hydroxy or imidazol-2-yl.

Examples of the silyl group in the 1-position in the above formulas are trimethylsilyl, triethylsilyl, tri-n-butylsilyl, methyldiisopropylsilyl, isopropyldimethylsilyl, triphenylmethyldimethylsilyl, dimethylphenylsilyl, ethyldiphenylsilyl, triphenylsilyl, t-butyldiphenylsilyl and the like. A preferred silyl group is represented by the following partial formula

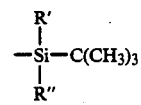

wherein R' and R" are straight chain $C_1-C_4$ alkyl radicals or phenyl. Especially preferred groups are represented when R' and R" are both methyl or ethyl. A preferred silyl group is dimethyl-t-butylsilyl.

Examples of $R_1'$ ester groups are benzyl, p-methoxybenzyl, p-nitrobenzyl, diphenylmethyl and like benzyl esters which are removable by hydrogenolysis or hydrolysis.

The compounds represented by formula 1 are prepared with the 4-formylazetidinone represented by the following structural formula

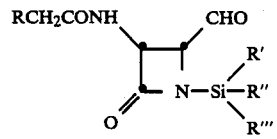

wherein R, R', R" have the same meanings as defined above for formula 1.

The compound of formula 1 wherein $R_1$ is an esterified 2-carboxyvinyl group is prepared with the 4-formylazetidinone and an ester of a di-($C_1-C_4$ alkyl)phosphononoacetic acid, for example, benzyl diethylphosphonoacetate. The reaction is carried out in an inert solvent such as acetonitrile in the presence of a tertiary amine, preferably a hindered tertiary amine such as diisopropylethylamine and a lithium halide, for example, lithium chloride. The reaction is carried out at room temperature and can be followed by thin layer chromatography on silica gel by employing ethyl acetate-hexane for elution. The 2-esterified carboxyvinyl substituted azetidinone represented by formula 1A above is obtained from the reaction mixture by conventional isolation procedures and is purified by chromatography over silica gel.

The intermediate 1A is converted by catalytic hydrogenation over palladium catalyst to the compound 1B. During the hydrogenation the ester group $R_1'$ is removed and the vinyl group of the 2-esterified carboxyvinyl substituent is reduced to provide the azetidinone 1B. The hydrogenation is carried out in an inert solvent such as tetrahydrofuran or an alcohol such as methanol or ethanol or mixtures of such solvents at an elevated hydrogen pressure of between about 40 and about 100 psi. The palladium catalyst employed may be any of those commonly employed for hydrogenation such as palladium metal itself or a supported palladium catalyst such as 5 or 10% palladium on carbon, palladium on barium carbonate and the like. The hydrogenation proceeds satisfactorily at room temperature and can be followed by hydrogen absorption. Following the reduction, the catalyst is removed by filtration, the solvent evaporated and the residue containing the product dissolved in a water immiscible solvent such as ethyl acetate. The product which is a free carboxylic acid is extracted from the solution with a base such as sodium bicarbonate or sodium carbonate and, following acidification of the aqueous extract, the free acid is extracted from the aqueous phase with a water immiscible solvent, for example, methylene chloride. Evaporation of the extract affords the compound represented by formula 1B wherein $R_2$ is hydroxy.

In the overall sequence of steps for converting the 4-formylazetidinone to the 1-carba(dethia)cephalosporin, the azetidinone 1B is converted to the 5-carboxypentane-3-one substituted azetidinone 1C as follows. The compound 1B wherein $R_2$ is hydroxy (the free carboxylic acid) is converted to 1B wherein $R_2$ is the imidazole-1-yl group by reacting the free acid form of 1B with carbonyl diimidazole in tetrahydrofuran. The imidazole-1-yl derivative is represented by the following structural formula.

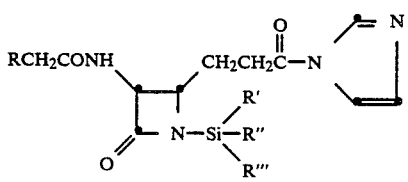

The N-acylimidazole 1B ($R_2$=imidazole-1-yl) is reacted in tetrahydrofuran or dimethylformamide or mixtures thereof with the magnesium salt of a half ester of malonic acid wherein the ester is an $R_1'$ ester group as defined above. The β-keto ester 1C is recovered from the reaction mixture by conventional methods. For example, the reaction mixture is evaporated under reduced pressure to obtain reaction product mixture as a residue which is dissolved in a mixture of a water-immiscible solvent such as ethyl acetate and aqueous sodium bicarbonate. The aqueous bicarbonate removes any unreacted free acid generated during the reaction. The organic layer is washed with carbonate, water and acid and is then dried and evaporated to provide the β-keto ester 1C.

The β-keto ester 1C is then converted by known procedures to the 1-carba(dethia)cephalosporin by following in general the procedures described by Evans et al. in U.S. Pat. No. 4,665,171. In carrying out the conversion of 1C, the 1-silyl group is removed by treating 1C in an inert solvent such as tetrahydrofuran with tetra-n-butylammonium fluoride to provide the NH azetidinone. The latter is reacted with an aryl sulfonyl azide such as p-toluenesulfonyl azide to provide via diazo transfer the 3-acylamino-4-(5esterified carboxy-4-diazopentane-3-one)azetidinone. The diazo intermediate is then cyclized in chloroform or other suitable solvent with a catalytic amount of rhodium tetraacetate. The product of the cyclization, 7β-phenylacetylamino, 7β-thienylacetylamino or 7β-phenoxyacetylamino-3-hydroxy-1-carba(dethia-3-cephem-4-carboxylic acid ester, may then be converted to the known 3-methoxy or 3-halo-1-carba(dethia)cephalosporin antibiotic compound.

The starting material employed in the preparation of the intermediates of this invention, namely, the 4-formylazetidinone represented by the foregoing formula, is obtained as the cis (±) racemate or as the enantiomeric cis (+) depending upon the method of preparation. The racemic form can be obtained as follows. Phthalimidoacetyl chloride is reacted with the enamine formed with anisidine and cinnamaldehyde to provide via cycloaddition the 1-(4-methoxyphenyl)-3β-pyhthalimido-4-(2-phenylvinyl)azetidin-2-one represented by the following structural formula

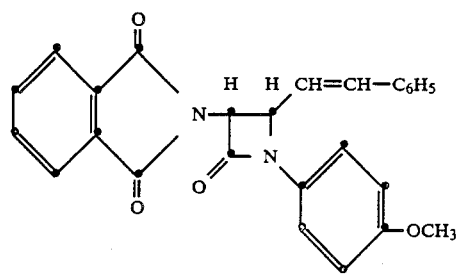

The phthaloyl group is removed from the cyclocondensation product with methylhydrazine to provide the corresponding 3β-aminoazetidinone. The latter can then be acylated with phenylacetyl chloride, thienylacetyl chloride or phenoxyacetyl chloride by standard coupling methods to provide the β-acylamino-4-(2-carboxyvinyl)-azetidin-2-one having the 4-methoxyphenyl group in the 1-position. The 4-methoxyphenyl group is then removed by known procedures with ceric ammonium nitrate to provide the 1H azetidinone represented by the following formula

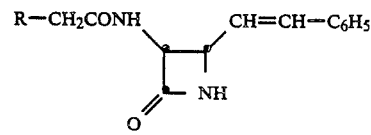

In the above formula, R has the same meaning as defined for formula 1. The NH azetidinone is then silylated with a chlorosilane represented by the formula

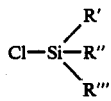

wherein R', R" and R'" have the same meaning as defined defined for formula 1. The N-silylated azetidinone is then reacted with ozone in an inert solvent, for example, a mixture of methyl alcohol and methylene chloride to provide the desired 4-formylazetidinone.

The cis(+)-4-formylazetidinone can be obtained as described by Evans et al. supra. The intermediates provided by this invention are thus valuable intermediates useful in the preparation of the 1-carba(dethia)cephalosporin antibiotic compounds.

This invention further provides the azetidinone represented by the following formula 2

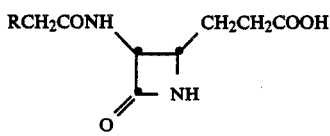

wherein R has the same meaning as defined for formula 1 above. The azetidinone 2 is obtained with azetidinone 1B wherein $R_2$ is hydroxy by removal of the 1-silyl group with acid, e.g., trifluoroacetic acid.

The azetidinone 2 is likewise useful in the preparation of 1-carba(dethia)-3-hydroxy-3-cephem esters. In this conversion, the azetidinone 2 is first esterified to provide the 4-(2-esterified)carboxyethylazetidinone and the latter alkylated in the 1-position with an ester of a haloacetic acid, e.g. t-butyl bromoacetate, to provide the compound represented by the following formula

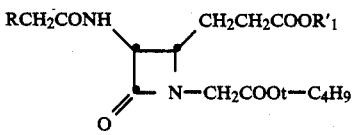

wherein R and $R_1'$ have the same meanings as defined for the formulae hereinabove. Following the alkylation of the NH azetidinone, the ester group $R_1'$ is removed and the free acid converted by known procedures to the phenylthio ester by reaction with thiophenol. The phenylthio ester derivative is then converted to 1-carba(dethia)-3-hydroxy-3-cephem as described by Hatanaki et al., *Tetrahedron Letters*, Vol. 24, No. 44, pp. 4837-4838, 1983.

Preferred intermediate compounds of the invention are represented by formula 1 wherein R is phenoxy, $R_1$ is 2-benzyloxycarbonylvinyl or 2-carboxyethyl, and the silyl group in the 1-position is dimethyl-t-butylsilyl. A further preferred compound of the invention is represented by the above formula 2.

The following examples further illustrate the present invention.

Preparation of
1-(t-Butyldimethylsilyl)-3β-phenoxyacetyl-amino-4β-formylazetidin-2-one Ozone was passed through a solution of 2.15 g of 1-t-butyldimethylsilyl-3β-phenoxyacetylamino-4β-(2-phenylvinyl)azetidin-2-one in 200 ml of methanol and 100 ml of methylene chloride at −78° C. for 15 minutes. The reaction mixture turned blue and excess ozone was dispelled. The reaction mixture was treated with 5 ml of dimethylsulfide and stirred for 1 hour at −78° C. The reaction mixture was evaporated under vacuum and the residue was triturated with hexane to remove the side product, benzaldehyde. The product, 1-(t-butyl-methylsilyl)-3β-phenoxyacetylamino-4β-formylazetidin-2-one, was obtained as a white solid and was used in the following reaction without further purification.

EXAMPLE 1

1-(t-Butyldimethylsilyl)-3β-phenoxyacetylamino-4-(2-benzyloxycarbonylvinyl)azetidin-2-one A solution of the 4-formylazetidin-2-one, obtained as described above, 0.23 g of lithium chloride, 0.7 g of diisopropylethylamine, and 1.55 g of benzyl diethylphosphonoacetate in 155 ml of acetonitrile was stirred at room temperature for 20 hours. The mixture was evaporated under vacuum and the residue chromatographed over silica gel with ethyl acetate-hexane. There were obtained 1.20 g (49% yield) of the title compound.

UV ($C_2H_5OH$) λ max 268 nm (ε2,005)
$^1$HNMR (300 MHz, DMSO-$d_6$) 6 8.96 (d, 1H, J =7 Hz), 7.4-7.1 (m, 6H), 7.0 (dd, 1H, J =15, 9 Hz), 6.94-6.85 (m, 4H), 6.1 (d, 1H, J=15 Hz), 5.3 (dd, 1H, J =7, 5 Hz), 5.12 (ABq, 2H), 4.4 (m, 9H), 0.95 (s, 9H) 0.11 (s, 3H) and 0.10 (s, 3H).
IR ($CHCl_2$) 3019, 1755, 1720, 1690, 1496, 1302, 1259, 1239, 1215 and 1173 cm$^{-1}$.
Elemental Analysis: $C_{27}H_{34}N_2O_5Si$: Theory: C, 65.56; H, 6.93; N, 5.66 Found: C, 65.55; H, 6.63; N, 5.86
Mass Spectrum: m/e 495 (M+)

EXAMPLE 2

1-(t-Butyldimethylsilyl)-3β-phenoxyacetylamino-4β-(2-carboxyethyl)azetidin-2-one A solution of 1.16 g of the product obtained in Example 1 in 200 ml of THF and 20 ml of ethanol was hydrogenated over 1.2 g of 5% Pd/C at room temperature for 6 hours under 60 psi hydrogen pressure. The reduction mixture was filtered and the filtrate evaporated under vacuum yielding 1.0 g of crude title compound having the following spectral characteristics:

UV ($C_2H_5OH$)λ max 289 nm (ε1,713)
IR ($CHCl_3$) 3500-2900 (br), 3018, 1734, 1690, 1523, 1496, 1257, 1237, 1215, 842 and 824 cm$^{-1}$
$^1$HNMR (300 MHz, $CDCl_3$) δ7.1-7.0 (m, 3H), 6.8-6.6 (m, 3H), 5.1 (dd, 1H, J=7, 5 Hz), 4.3 (s, 2H), 3.6 (m, 1H), 2.0-1.8 (m, 3H), 1.4 (m, 1H), 0.8 (s, 9H), 0.05 (s, 3H), 0.02 (s, 3H).
Elemental Analysis: $C_{20}H_{30}N_2O_5Si$; Theory: C, 59 09; H, 7.44; Found: C, 59.10; H, 7.35; N, 6.63

The product was dissolved in a mixture of ethyl acetate and saturated aqueous sodium bicarbonate. The aqueous layer was separated, washed with ethyl acetate, acidified with concentrated HCl, and extracted with methylene chloride. The extract was dried over sodium sulfate, filtered and evaporated under vacuum, yielding 0.5 g of the title compound as a white solid.

EXAMPLE 3

1-(t-Butyldimethylsilyl)-3β-phenoxyacetylamino-4β-[2-(imidazol-1-ylcarbonyl)ethyl]azetidin-2-one A solution of 500 mg (1.23 mmole) of 1-(t-butyldimethylsilyl)-3β-phenoxyacetylamino-β-(2-carbonxyethyl- )azetidin-2-one and 360 mg (2.22 mmole) of carbonyl imidazole in 25 ml of tetrahydrofuran was stirred at room temperature for 16 hours.

EXAMPLE 4

1-(Dimethyl-t-butylsilyl)-3β-phenoxyacetylamino-4β-(5-p-nitrobenzyloxycarbonylpentan-3-one)azetidin-2-one A solution of acylimidazole derivative prepared as described by Example 3 and 1.11 g (2.22 mmole) of the magnesium salt of the half p-nitrobenzyl (PNB) ester of malonic acid, $Mg^+$ $(PNBOC(O)CH_2CO_2^-)_2$, in tetrahydrofuran (25 ml) was stirred at room temperature for 20 hours. The solvent was removed by evaporation under vacuum and the residue dissolved in a mixture of ethyl acetate and saturated aqueous sodium bicarbonate. The ethyl acetate layer was separated, washed with aqueous sodium bicarbonate, water, 1N HCl and with brine, dried over sodium sulfate, filtered and evaporated under vacuum to yield the title compound as a yellow oil. The product was purified via preparative thin layer chromatography on silica gel plates using toluene:ethyl acetate, 1:1, v:v. There were obtained 509.7 mg of the β-keto ester title compound.

$^1$HNMR (300 MHz) δ 6 8.2 (d, 2H, J=8 Hz), 8.0 (d, 1H, J=7 Hz), 7.6–6.8 (m, 5H), 5.25 (m, 3H), 4.6 (s, 2H), 3.6 (m, 3H), 2.5 (m, 2H), 2.4–1.8 (m, 2H), 1.0 (s, 9H), 0.3 (s, 3H), 0.28 (s, 3H).

EXAMPLE 5

3β-Phenoxyacetylamino-4β-(2-carboxyethyl)azetidin-2-one

The saturated acid prepared as described by Example 2 (20 mg of crude) was dissolved in 5 ml of methanol and 1 ml of trifluoroacetic acid was added. The solution was stirred for 4 hours at room temperature. The reaction mixture is evaporated under vacuum to remove the solvent and acid and the residue is triturated with hexane/ether and dried to provide the title compound, 3β-phenoxyacetylamino-4β-(2-carboxyethyl) azetidin-2-one.

Mass Spectrum: m/e 293 (M+)

Elemental Analysis: $C_{14}H_{16}N_2O_5$: Theory: C, 57.53; H, 5.52; N, 9.58; Found: C, 56.28; H, 5.44; N, 9.19

IR (KBr): 3600-2900 (br), 3332, 3050, 1742, 1713, 1665, 1601, 1535, 1489, 1443, 1400, 1290, 1247, 1235, 1194, 1113, 1083, 1064, 862, 837 and 804 cm$^{-1}$ $^1$HNMR (300 MHz, DMSO-d$_6$) δ 12.2 (s, 1H), 8.9 (d, 1H, J=7 Hz), 8.3 (s, 1H), 7.3 (m, 2H), 6.9 (m, 3H), 5.1 (dd, 1H, J=5, 7 Hz), 4.6 (ABq, 2H), 3.65 (m, 1H), 2.2 (m, 2H) and 1.6 (m, 2H).

EXAMPLE 6

Preparation of p-nitrobenzyl 7β-phenoxyacetylamino-3-hydroxy-1-carba(dethia-3-cephem-4-carboxylate

A. Removal of N-silyl group

A solution, 490 mg (0.84 mmole) of 1-(dimethyl-t-butylsilyl)-3β-phenxoyacetylamino-4β-(5-p-nitrobenzyloxycarbonylpentan-3-one) azetidin-2-one (prepared as described by Example 4), in 30 ml of THF was cooled to −78° C. and 1.26 ml of a 1M solution of tetra-n-butylammonium fluoride in THF was added. The solution was stirred at −78° C. for 15 minutes and then was poured into water. The aqueous mixture was extracted with ethyl acetate and the extract washed with brine, dried over sodium sulfate, filtered and evaporated to dryness. The residue was suspended in methylene chloride, the suspension diluted with hexane and the white precipitate of product filtered and dried. There were obtained 520 mg of the de-silyl azetidinone β-keto ester, 3β- phenoxyacetylamino-4β-(5-p-nitrobenzyloxycarbonylpentan-3-one) azetidinone as a white solid.

B. Diazo Transfer

To a suspension of 500 mg (1.066 mmole) of the azetidinone β-keto ester and 500 mg (2.15 mmole) of p-carboxybenzenesulfonyl azide in 100 ml of acetonitrile was added at room temperature with stirring 1.5 ml of diisopropylethylamine. The mixture was stirred for one and was evaporated under vacuum to dryness. The residue was dissolved in methylene chloride and the solution washed with a saturated solution of sodium bicarbonate, dried over sodium sulfate, filtered and evaporated under vacuum to yield the diazo product, 3β-phenoxyacetylamino-4β-(5-p-nitrobenzyloxycarbonyl-4-diazopentan-3-one) azetidinone.

The product was suspended in methylene chloride and precipitated by addition of diethyl ether to the suspension. The precipitate was filtered and dried to yield 510 mg of the product.

C. Diazo Insertion

The diazo compound, 10 mg, was dissolved in 10 ml of chloroform (filtered through alumina prior to use and a catalytic amount of rhodium tetraacetate was heated at the reflux temperature for 20 minutes. The product is isolated as the 3-trifluoromethylsulfonyloxy derivative by treating the cooled 0° C. reaction mixture with excess triflic anhydride and diisopropylethylamine for about 20 minutes. The solvent is removed by evaporation under vacuum and 3-triflate-1-carba-3-cephem is purified by preparative thin layer chromatography on a silica gel plate using toluene:ethyl acetate, 1:1, v:v.

We claim:

1. A compound of the formula $$R-CH_2CONH\begin{array}{c}H\ \ H\\ \underset{\underset{O}{\|}}{\fbox{\phantom{XX}}}\end{array}\begin{array}{c}R_1\\ N-Si-R''\\ R'''\end{array}$$

wherein R is phenyl, phenoxy or thienyl; $R_1$ is —$CH_2CH_2$—$COR_2$, $R_2$ is hydroxy, imidazol-1-yl or a carboxy-protecting group; and R', R" and R'" independently are $C_1$-$C_4$ alkyl, aryl, or aralkyl.

2. The compound of claim 1 wherein R' and R" are both $C_1$-$C_4$ alkyl or phenyl and R'" is t-butyl.

3. The compound of claim 1 wherein R is phenoxy.

4. The compound of claim 3 which is 1-(dimethyl-t-butylsilyl)-3β-phenoxyacetylamino-4β-(2-carboxyethyl)azetidin-2-one.

5. The compound of claim 1 wherein R is phenyl.

6. The compound of the formula $$R-CH_2CONH\diagdown\ \ \diagup CH_2CH_2COOH\\ \phantom{XXX}\fbox{\phantom{XX}}\\ O\diagup\ \ \diagdown NH$$

wherein R is phenyl or phenoxy.

* * * * *